United States Patent
Gutsmann et al.

(10) Patent No.: US 8,889,725 B2
(45) Date of Patent: Nov. 18, 2014

(54) SUGAR-BASED BAIT

(75) Inventors: Volker Gutsmann, Langenfeld (DE); Thomas Böcker, Leichlingen (DE); Günther Nentwig, Leverkusen (DE); Justin McBeath, Woodland (AU); Jeffery Einam, Victoria Point (AU)

(73) Assignee: Bayer Cropscience AG, Monheim (DE)

( * ) Notice: Subject to any disclaimer, the term of this patent is extended or adjusted under 35 U.S.C. 154(b) by 1689 days.

(21) Appl. No.: 12/282,275

(22) PCT Filed: Mar. 8, 2007

(86) PCT No.: PCT/EP2007/001985
§ 371 (c)(1),
(2), (4) Date: Jul. 6, 2009

(87) PCT Pub. No.: WO2007/104461
PCT Pub. Date: Sep. 20, 2007

(65) Prior Publication Data
US 2009/0304624 A1  Dec. 10, 2009

(30) Foreign Application Priority Data
Mar. 11, 2006  (DE) .......................... 10 2006 011 403

(51) Int. Cl.
*A01N 43/50* (2006.01)
*A01N 25/00* (2006.01)

(52) U.S. Cl.
CPC .................................. *A01N 25/006* (2013.01)
USPC ........... 514/397; 514/398; 514/400; 424/405; 426/1

(58) Field of Classification Search
None
See application file for complete search history.

(56) References Cited

U.S. PATENT DOCUMENTS 6,245,327 B1 * 6/2001 Faehl et al. ..................... 424/84
2004/0057976 A1 * 3/2004 Warner et al. ................. 424/410

FOREIGN PATENT DOCUMENTS

EP  0 084 310  7/1983

OTHER PUBLICATIONS

Scharf et al., Impacts of Residual Insecticide Barriers on Perimeter-Invading Ants, with Particular Reference to the Odourous House Ant, *Tapinoma sessile*, J. Econ. Entomol. (2004), vol. 97, No. 2, pp. 601-605.*
STN online, file BIOSIS, Acc. No. 1944:7636, Doc. No. PREV19441800007656 (Erdmuthe, Zeitschr. Angew. Ent. (1942), vol. 29, No. 2, pp. 244-281), Abstract.*
About Us History of Karo, [online], [retrieved on Oct. 11, 2011]. Retrieved from the Internet:< URL: http://www.karosyrup.com/Karo_History.pdf>.*
Product Specification; Primatin R KS-03; Special Sugar Syrup; Valid From Sep. 13, 2011; Version 5; Pfeifer & Langen.
Produktspezifikation; P & L—Invertix R 80/95 PM; Invertzuckersirup; Version 2; Valid From Jul. 8, 2004; Pfeifer & Langen.
Product Specification; Invertix R 72,2/66; Invert Sugar Syrup White; Version 3; Valid From Sep. 13, 2011; Pfeifer & Langen.
Product Specification; Invertix R 81/55; Invert Sugar Syrup; Version 09; Valid From Sep. 13, 2011; Pfeifer & Langen.
Glucose Syrup EM 38 = 43; HELLMI, (2006).
Maxforce Quantum Brochure; Bayer Environmental Science; 4 Pages, (2009).
Ant Control Gets Faster Bayer'S Maxforce Quantum Approved; May & Jun. 2009; www.pestmagazine.co.uk; Pest; p. 28 and 29.
Winter Ant Baiting Inside Structures With Maxforce; Bayer Environmental Science; vol. 8; No. 1; Jan. 12, 2011.
Rupes et al.; "A Novel Imidacloprid Bait for Control of *Monomorium pharaonis* (Hymenoptera: Formicidae)"; 2008; pp. 77-84.
Brooks et al.; "Elimination of a *Tapinoma melanocephalum* (Hymenoptera: Formicidae) Infestation Using Imidacloprid Bait"; 2008; pp. 219-223.

* cited by examiner

*Primary Examiner* — Abigail Fisher
*Assistant Examiner* — Frank Choi
(74) *Attorney, Agent, or Firm* — Miles & Stockbridge P.C.

(57) ABSTRACT

An ant bait which contains an active substance having insecticidal activity and a sugar syrup is described.

14 Claims, No Drawings

SUGAR-BASED BAIT

CROSS REFERENCE TO RELATED APPLICATIONS

This application is a §371 National Stage Application of PCT/EP2007/001985 filed Mar. 8, 2007 which claims priority to German Application 10 2006 011 403.5 filed Mar. 11, 2006.

BACKGROUND OF THE INVENTION

1. Field of the Invention

The present invention relates to sugar syrup-based ant baits, to a process for the production of these ant baits and to their use.

2. Description of Related Art

It is known that insecticides can be employed in a wide variety of preparation forms in the control of ants. For example, mention may be made of spray compositions, dusts, spray cans and baits. Since ants are often found within fairly close living range of humans and of domestic animals and must be controlled there, bait preparations are increasingly gaining in importance because of their comparatively low endangerment of humans and domestic animals and because of their very generally high environmental friendliness. Furthermore, baits containing a slow-acting insecticide make possible introduction into the nest by the ants. Feeding to further harvesting ants, queen(s) and larvae (trophallaxis) leads to complete eradication of the colony, which can scarcely be achieved using other processes.

The number of insecticidal active substances which are suitable for use in an ant bait, however, is very low, since the ants, which react very sensitively, usually refuse their acceptance. This applies particularly if the baits have to contain active substances in high concentrations in order to achieve a satisfactory high activity.

As insecticidally and acaricidally active substances which can be employed for the control of ants, for example, O,O-diethylthionophosphoryl-α-oximinophenylacetonitrile (phoxim) and O,O-diethylthionophosphoryl-α-oximino-(2-chlorophenyl)acetonitrile (chlorphoxim) have already been known for many years (cf. German Patent Specification 1 238 902). These substances can be applied in the form of spray and dust compositions.

It has furthermore been attempted to employ phoxim for the control of ants in the form of a bait formulation (cf. "Toxicological and Biological Studies of Odorous House Ant, Tapinoma sessile" in Joum, of econ. Ent. Vol. 63, 1971-1973 (1970)). It resulted here that complete control of the ants can be achieved by means of baits which contain 0.05% by weight of phoxim as a mixture with blackberry syrup or blackberry jam. It is disadvantageous, however, that baits having such a low content of phoxim do not have sufficiently long storage stability for practical purposes. Analogous baits, in which the phoxim is present in a concentration of 0.5% by weight to 1% by weight, indeed have a stability and a duration of action sufficient for practical purposes, but exhibit a repellent action, so that the ants do not feed on these baits. The use of baits which contain phoxim has thus not yielded the desired success in ant control up to now. Finally, phoxim acts relatively rapidly, so that the trophallaxis described above does not occur or occurs only to a small extent.

Ant baits which also contain glycerol and/or honey in addition to phoxim and/or chlorphoxim, which however, also do not satisfactorily solve the disadvantages described above, are furthermore known from EP-A1-0 084 310.

An additional difficulty in the production of phoxim- and/or chlorphoxim-based baits lies in the fact that the active substances are relatively temperature-sensitive. Therefore the implementation of the customary production method, which consists in blending and warming the components in order to reduce the viscosity of the corresponding mixture and to make it more easily stirrable, has to be ruled out.

It has moreover emerged that ants particularly prefer liquid baits. The intake of liquid baits is simplest, and thus preferred, for the harvesting ants, which are specialized in the search for and assimilation of food. A disadvantage of liquid baits, however, is that the water content after application can fall to zero due to evaporation (drying out). This phenomenon has a disadvantageous effect on the consumption of the bait by the ant, due to the solidification of the bait and also due to concentration of the active substance contained (repellent effect). For the reasons mentioned, liquid baits are indeed very attractive initially (for 24 h), but they then lose their action rapidly.

SUMMARY OF THE INVENTION

Thus, there is furthermore a need for ant baits which do not have the disadvantages previously described. In particular, there is a need for ant baits which can be willingly consumed at the same time by a large number of different ants, and after application, are attractive and thus highly active for a sufficiently long period of time for the ants and are stable on storage, cost-effective and simple to produce.

This object is achieved by an ant body which contains at least one active substance having insecticidal activity and sugar syrup.

According to the invention, it has been found that ants baits which in addition to at least one insecticidal active substance, also contain sugar syrup, are highly effective for the control of ants and at the same time remain attractive for the ants over a long period of time.

In a first embodiment of the present invention, the ant body additionally contains an embittering substance, such as, for example Bitrex®.

In a second embodiment of the present invention, the ant body according to the invention essentially consists of the at least one active substance having insecticidal activity, sugar syrup and optionally the embittering substance.

DETAILED DESCRIPTION OF A PREFERRED EMBODIMENT

The insecticidal active substance which is used in the ant baits according to the invention is fundamentally subject to no restriction inasmuch as it is able to destroy ants. The insecticidal active substance is therefore preferably selected from the group consisting of acetylcholinesterase (AChE) inhibitors,
  carbamates,
    for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate
  organophosphates,
    for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulfone, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion sodium channel modulators/voltage-dependent sodium channel blockers
    pyrethroids,
        for example acrinathrin, allethrin (d-cis-trans, d-trans), beta-cyfluthrin, bifenthrin, bioallethrin, bioallethrin S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (-1R-isomer), tralomethrin, transfluthrin, ZXI 8901, pyrethrins (pyrethrum)
    DDT
    oxadiazines,
        for example indoxacarb
    semicarbazones,
        for example metaflumizon (BAS3201)

acetylcholine receptor agonists/antagonists
    chloronicotinyls,
        for example acetamiprid, clothianidin, dinotefuran, imidacloprid, nitenpyram, nithiazine, thiacloprid, thiamethoxam
    nicotine, bensultap, cartap acetylcholine receptor modulators
    spinosynes,
        for example spinosad GABA-controlled chloride channel antagonists
    organochlorines,
        for example camphechlor, chlordane, endosulfan, gaamma-HCH, HCH, heptachlor, lindane, methoxychlor
    fiprols,
        for example acetoprole, ethiprole, fipronil, pyrafluprole, pyriprole, vaniliprole chloride channel activators
    mectins,
        for example abamectin, emamectin, emamectin benzoate, ivermectin, lepimectin, milbemycin juvenile hormone mimetics,
    for example diofenolan, epofenonane, fenoxycarb, hydroprene, kinoprene, methoprene, pyriproxifen, triprene ecdysone agonists/disrupters
    diacylhydrazines,
        for example chromafenozide, halofenozide, methoxyfenozide, tebufenozide inhibitors of chitin biosynthesis
    benzoylureas,
        for example bistrifluron, chlofluazuron, diflubenzuron, fluazuron, flucycloxuron, flufenoxuron, hexaflumuron, lufenuron, novaluron, noviflumuron, penfluoron, teflubenzuron, triflumuron
    buprofezin
    cyromazine inhibitors of oxidative phosphorylation, ATP disrupters
    diafenthiuron
    organotin compounds,
        for example azocyclotin, cyhexatin, fenbutatin oxide uncouplers of oxidative phosphorylation by interruption of the H-proton gradient
    pyrroles,
        for example chlorfenapyr
    dinitrophenols,
        for example binapacyrl, dinobuton, dinocap, DNOC site I electron transport inhibitors
    METIs,
for example fenazaquin, fenpyroximate, pyrimidifen, pyridaben, tebufenpyrad, tolfenpyrad
    hydramethylnon
    dicofol site II electron transport inhibitors
    rotenones site III electron transport inhibitors
    acequinocyl, fluacrypyrim microbial disrupters of the insect intestinal membrane
    *Bacillus thuringiensis* strains inhibitors of lipid synthesis
    tetronic acids,
        for example spirodiclofen, spiromesifen
    tetramic acids,
        for example spirotetramate
    carboxamides,
        for example flonicamid
    octopaminergic agonists,
        for example amitraz inhibitors of magnesium-stimulated ATPase,
    propargites
    nereistoxin analogs,
        for example thiocyclam hydrogen oxalate, thiosultap-sodium agonists of the ryanodin receptor,
    benzoic acid dicarboxamides,
        for example flubendiamid
    anthranilamides,
        for example DPX E2Y45 (3-bromo-N-{4-chloro-2-methyl-6-[(methylamino)carbonyl]-phenyl}-1'-(3-chloropyridin-2-yl)-1H-pyrazole-5-carboxamide)

biologicals, hormones or pheromones
    azadirachtin, *Bacillus* spec., *Beauveria* spec., codlemone, *Metarrhizium* spec., *Paecilomyces* spec., thuringiensin, *Verticillium* spec.

active substances having unknown or nonspecific mechanisms of action
    mite growth inhibitors,
        for example clofentezine, etoxazole, hexythiazox amidoflumet, benclothiaz, benzoximate, bifenazate, bromopropylate, buprofezin, quinomethionate, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin.

Beside individual active substances, combinations of 2 or more active substances can be employed. In addition, combination with synergists, e.g. piperonyl butoxide, MGK 264 (Octacide) or Sesamex is possible.

Furthermore, attractants such as sex pheromones, aggregation pheromones and aromatic substances (synthetic, naturally identical or natural) can be employed.

Among the insecticidal active substances, representatives of the chloronicotinyls and the fiproles are particularly preferred. In the context of the present invention, imidacloprid (1-(6-chloro-3-pyridinylmethyl)-N-nitroimidazolidin-2-ylidenamine) and fipronil (5-amino-1-[2,6-dichloro-4-(trifluoromethyl)phenyl]-4-[(trifluoromethyl)sulfinyl]-1H-pyrazole-3-carbonitrile) are very particularly preferred as insecticidal active substances.

The content of insecticidal active substance in the ant body according to the invention is dependent on the nature of the active substance and can therefore vary within large ranges. In general, as much insecticidal active substance is used as is necessary in order to destroy ants. In particular with respect to imidacloprid, it has emerged as being advantageous if the content of imidacloprid is 0.001 to 0.5% by weight, particularly preferably 0.001 to 0.3% by weight, in particular 0.001 to 0.1% by weight, in each case based on the ant bait.

Fundamentally, the sugar syrup which is used in the ant baits according to the invention is subject to no restrictions and all possible forms of sugar syrup can be used.

It has emerged as preferable if the sugar syrup used is sucrose and/or the monosaccharide contains glucose and fructose and/or their dimers, oligomers, polymers. The mixing ratios of the previously mentioned carbohydrate components are widely variable. Possible mixing ratios are illustrated in more detail by means of the following examples, but are in no case restricted to these examples: for an invert syrup, in the dry matter 34% sucrose, 33% fructose, 33% glucose; for a corn syrup, in the dry matter glucose 36%, maltose 31%, maltotriose 13%, oligosaccharides 20%; for an enzymatic modified grain syrup fructose 42%, glucose 52%, maltose 3%, oligosaccharides 3%.

It has additionally emerged as preferable if the sugar syrup used has a content of dry matter of preferably 50% to 95%, particularly preferably 60 to 90%, in particular 65 to 90%. The pH of the sugar syrup is preferably in a range from 2 to 8, particularly preferably 2.5 to 7.5, in particular 3.0 to 7.0.

In the context of the present invention, a sugar syrup is understood as meaning an aqueous sugar syrup which, in addition to the dry weight of sugar, additionally contains water.

In the context of the present invention, for example, invert sugar and glucose syrup, preferably having the previously defined specifications, can be used.

In general, various sugar syrups are also unequally willingly consumed by various ant species. It has therefore proven advantageous if the sugar syrup used is basic invert syrup. Of these, the basic invert syrup INVERTIX® 72.7/66 is particularly preferred and INVERTIX® 81/55, which is especially preferred by most ant species. In this connection, it is particularly interesting in the context of the present invention that *Monomorium pharaonis* (Pharaoh ant) accepts this syrup very well, since in this species protein preference is in general assumed.

A further sugar syrup which can preferably be used in the context of the present invention is corn syrup, for example Karo® Light Corn Syrup from Karo. This sugar syrup is a sugar syrup which contains light corn syrup, high fructose corn syrup, salt(s) and vanilla flavor.

The production of the ant baits according to the invention is subject to no particular restriction in the context of the present invention. In general, production is carried out in such a way that the insecticidal active substance, optionally with the addition of the amount of embittering substance intended according to the invention, optionally of the synergists according to the invention and/or of the attractants optionally intended according to the invention, is stirred into the ant syrup.

The ant baits according to the invention have the advantage that they are consumed by a large number of different ants. At the same time, the ant baits according to the invention are stable for a long period of time after its application, which is confirmed by way of example in the working examples. At the same time, their production is simple and cost-effective.

The bait materials according to the invention can be applied, in the control of ants, in all forms customary for such bait formulations. Examples of the various application forms which may be mentioned: unconcealed application of the liquid from a syringe or tube in the vicinity of an ant trail or of an ants' nest; concealed application of the liquid from a syringe or tube in cracks and gaps in the vicinity of an ant trail or of an ants' nest (gaps in walls, gaps in paving stones, gaps in wood, etc) and protected application in a bait station. The stations are designated as all containers customary in the trade, which protects the user from contact with insecticide-containing products, is hermetically sealed before use and is easily accessible for the ants after use and prevents the emergence of the formulation by means of suitable construction.

According to the invention, unconcealed application of the liquid to an ants' nest from a syringe or tube is likewise possible.

With the aid of the abovementioned application forms, ants can be controlled both in the housekeeping and hygiene field and in agriculture and in gardening or horticulture in all places where they are undesirable. The procedure here is to apply the baits according to the invention to the places infested by ants.

The hygiene field especially also comprises pest control by professional pest control technicians.

The present invention moreover relates to the use of sugar syrups in ant baits. The present invention especially relates to the use of sugar syrups in ant baits which are employed for destroying ants. With respect to the specific selection of sugar syrups, the remarks made above apply for the sugar syrup in the ant baits according to the invention.

The present invention is illustrated in more detail by means of the following examples, but is in no case restricted to these examples.

Example 1

Assimilation of Different Ant Syrups by Various Ant Species

Different ant baits, which differ in the selection of the sugar syrup, are used on different ants for the determination of the activity. The results obtained are shown in Table 1 below

TABLE 1

| Compound | Lasius niger Assimln | Lasius niger Percent | Linepithema humile Assimln | Linepithema humile Percent | Monomorium pharaonis Assimln | Monomorium pharaonis Percent | Tapinoma melanocephalum Assimln | Tapinoma melanocephalum Percent |
|---|---|---|---|---|---|---|---|---|
| Invertix 80/95 PM | 113.5 mg | 13.0% | 48.1 mg | 19.4% | 154.5 mg | 15.6% | 153.3 mg | 13.4% |
| Invertix 81/55 PM | 126.7 mg | 14.5% | 62.2 mg | 25.1% | 214.2 mg | 21.6% | 274.5 mg | 24.1% |
| Invertix 72.7/66 PM | 459.5 mg | 52.5% | 70.6 mg | 28.3% | 350.6 mg | 35.2% | 315.2 mg | 27.7% |
| Primatin KS-03 | 161.6 mg | 18.5% | 49.8 mg | 20.1% | 192.8 mg | 19.4% | 274.0 mg | 24.0% |
| Glucose Syrup 43° | 12.7 mg | 1.5% | 17.6 mg | 7.1% | 81.4 mg | 8.2% | 123.6 mg | 10.8% |
| Total | 874.0 mg | 100% | 248.3 mg | 100% | 993.5 mg | 100% | 1140.6 mg | 100% |

The results presented in Table 1 show that different syrups are consumed to different extents by various species of ants. The invert syrup 72.7/66 preferably used according to the invention is, however, preferred by all species of ants. The fact is also particularly interesting that *Monomorium pharaonis* (Pharaoh ant) accepts this syrup very readily, as in this species in general a protein preference is assumed.

The invert syrup 81/55 preferred according to the invention is also readily accepted by all species of ants.

Experiment 2

Attractiveness of the Ant Baits According to the Invention after Application

TABLE 2

| Compound | Lasius niger Consumption | Monomorium pharaonis Consumption |
|---|---|---|
| Invertix 72.7/66 PM fresh | 508.7 mg | 91.5 mg |
| Invertix 72.7/66 PM 2 weeks old | 248.5 mg | 136.3 mg |

Table 2 shows that the invert syrup preferred according to the invention is also still readily accepted by two important species of ants after 2 weeks unconcealed application.

TABLE 3

| Compound | Lasius niger Consumption | Linepithema humile Consumption |
|---|---|---|
| Invertix 81/55 PM fresh | 126.7 mg | 62.2 mg |
| Invertix 81/55 PM 1 week old | 117.7 mg | 78.5 mg |

Table 3 shows that the invert syrup 81/55 likewise preferred according to the invention is also still readily accepted by two important species of ants after one week's unconcealed application.

*Lasius niger*—small black ant
*Linepithema humile*—Argentine ant
*Monomorium pharaonis*—Pharaoh ant
*Tapinoma melanocephalum*—ghost ant

TABLE 4

Field trial test against Pharaoh ants

| Days after treatment | Number of cases with ants | Number of ants per case |
|---|---|---|
| −15 days | 9 | 19 |
| 0 | 12 | 24 |
| 14 days | 0 | 0 |
| 36 days | 0 | 0 |
| 65 days | 0 | 0 |
| 99 days | 0 | 0 |

Invertix 81/55 containing 0.05% imidacloprid

The example in Table 4 shows that the invert syrup 81/55 likewise preferred according to the invention also brings about a rapid and lasting control of ants, in this case *Monomorium pharaonis*, in field tests. An apartment house infested with Pharaoh ants was investigated. Ant traps were laid out in order to carry out an infestation determination. 14 days after the treatment, ants were no longer trapped. This state of affairs did not change in the observation period. The treatment success was thus 100%.

The invention claimed is:

1. An ant bait consisting essentially of at least one active substance having insecticidal activity and sugar syrup,
   wherein imidacloprid is the active substance having insecticidal activity and the content of imidacloprid in the ant bait is 0.001 to 0.1% by weight, based on the total weight of the ant bait, and
   wherein the sugar syrup is an invert sugar syrup, and has a content of dry matter of 65% to 81% and a sugar inversion degree of 55% to 66%.

2. The ant bait as claimed in claim 1, wherein the ant bait additionally comprises at least one embittering agent.

3. An ant bait according to claim 1, with the proviso that the ant bait does not comprise proteins.

4. An ant bait according to claim 1, wherein the bait is still attractive to ants two weeks after application.

5. An ant bait according to claim 1, wherein the sugar syrup has a content of dry matter of 72.7% and a sugar inversion degree of 66%.

6. An ant bait according to claim 1, wherein the sugar syrup has a content of dry matter of 81% and a sugar inversion degree of 55%.

7. A process for the production of an ant bait as claimed in claim 1, comprising mixing imidacloprid with the sugar syrup, optionally with addition of an embittering agent.

8. A method for the control of ants comprising utilizing an ant bait according to claim 1.

9. A method according to claim 8, wherein the ant bait is applied in the vicinity of an ant trail or an ant's nest.

10. A method according to claim 9, wherein the ant bait is applied in an unconcealed application from a syringe or tube in the vicinity of an ant trail or an ant's nest.

11. A method according to claim 9, wherein the ant bait is applied in a concealed application from a syringe or tube in cracks and gaps in the vicinity of an ant trail or an ant's nest.

12. A method according to claim 9, wherein the ant bait is applied in protected application in a bait station.

13. A method according to claim 9, wherein the ants are *Lasius niger* species, *Linepitherma humile* species, *Monomorium pharaonis* species, or *Tapinoma melanoephalum* species.

14. A method for the control of ants comprising utilizing an ant bait according to claim 2.

* * * * *